(12) United States Patent
Blamey

(10) Patent No.: US 6,517,581 B2
(45) Date of Patent: Feb. 11, 2003

(54) METHOD AND APPARATUS FOR PREPARING A FEMUR TO RECEIVE A MODULAR PROSTHETIC FEMORAL COMPONENT

(75) Inventor: Jonathan Blamey, Macclesfield (GB)

(73) Assignee: Zimmer, Inc., Warsaw, IN (US)

( * ) Notice: Subject to any disclaimer, the term of this patent is extended or adjusted under 35 U.S.C. 154(b) by 14 days.

(21) Appl. No.: 09/770,009

(22) Filed: Jan. 25, 2001

(65) Prior Publication Data

US 2002/0133233 A1 Sep. 19, 2002

(51) Int. Cl.[7] ............................ A61F 2/32; A61B 17/32
(52) U.S. Cl. ...................... 623/22.12; 606/80; 606/172
(58) Field of Search .......................... 606/79, 80, 85, 606/84, 172, 180; 30/352; 451/48; 623/22.12

(56) References Cited

U.S. PATENT DOCUMENTS

| | | | | |
|---|---|---|---|---|
| 5,190,548 A | * | 3/1993 | Davis | 606/80 |
| 5,562,673 A | * | 10/1996 | Koblish et al. | 606/80 |
| 5,573,537 A | * | 11/1996 | Rogozinski | 606/80 |
| 5,607,431 A | * | 3/1997 | Dudasik et al. | 606/80 |
| 5,667,509 A | * | 9/1997 | Westin | 606/80 |
| 5,908,423 A | * | 6/1999 | Kashuba et al. | 606/80 |
| 5,941,706 A | * | 8/1999 | Ura | 433/165 |
| 5,951,561 A | * | 9/1999 | Pepper et al. | 606/80 |

\* cited by examiner

Primary Examiner—Jeffrey A. Smith

(74) Attorney, Agent, or Firm—Jacque R. Wilson

(57) ABSTRACT

The present invention provides an improved method and apparatus for preparing a femur to receive a modular prosthetic femoral component. A distal reamer having a plurality of sets of depth marks is utilized to prepare the distal femoral canal. The sets of depth marks on the distal reamer correspond in number to the number of distal femoral stems available for use with the particular modular prosthetic femoral implant set. Each set of depth marks comprises a plurality of indicator rings corresponding in number to the number of proximal bodies adapted for utilization with the prosthetic femoral component set. Prior to distal reaming, the appropriate set of depth marks and indicator ring is chosen corresponding to the modular components the surgeon wishes to utilize. Reaming then takes place until the chosen indicator ring is aligned with a reference point (e.g., the top of the greater trochanter). Upon reaching the appropriate reaming depth, the distal reamer is left in place in the femoral canal. A cannulated forming tool, e.g. a rasp or reamer, is thereafter positioned over the shank of the distal reamer and utilized to effect proximal canal sizing. The distal reamer head is sized whereby the proximal reamer, e.g., will abut the reaming head of the distal reamer when the proximal reamer reaches the appropriate depth associated with the shortest distal stem of the modular femoral component set. In this way, the head of the distal reamer provides a mechanical stop for the proximal reamer so that both under reaming and over reaming are avoided. In cases in which a longer femoral stem is utilized, a cylindrical spacer having a length corresponding to the length difference between the shortest distal stem and the chosen distal stem is utilized to provide a mechanical stop for the proximal reamer. The reamer spacer includes an elongate aperture sized whereby the reamer spacer fits about the shank of the distal reamer.

19 Claims, 8 Drawing Sheets

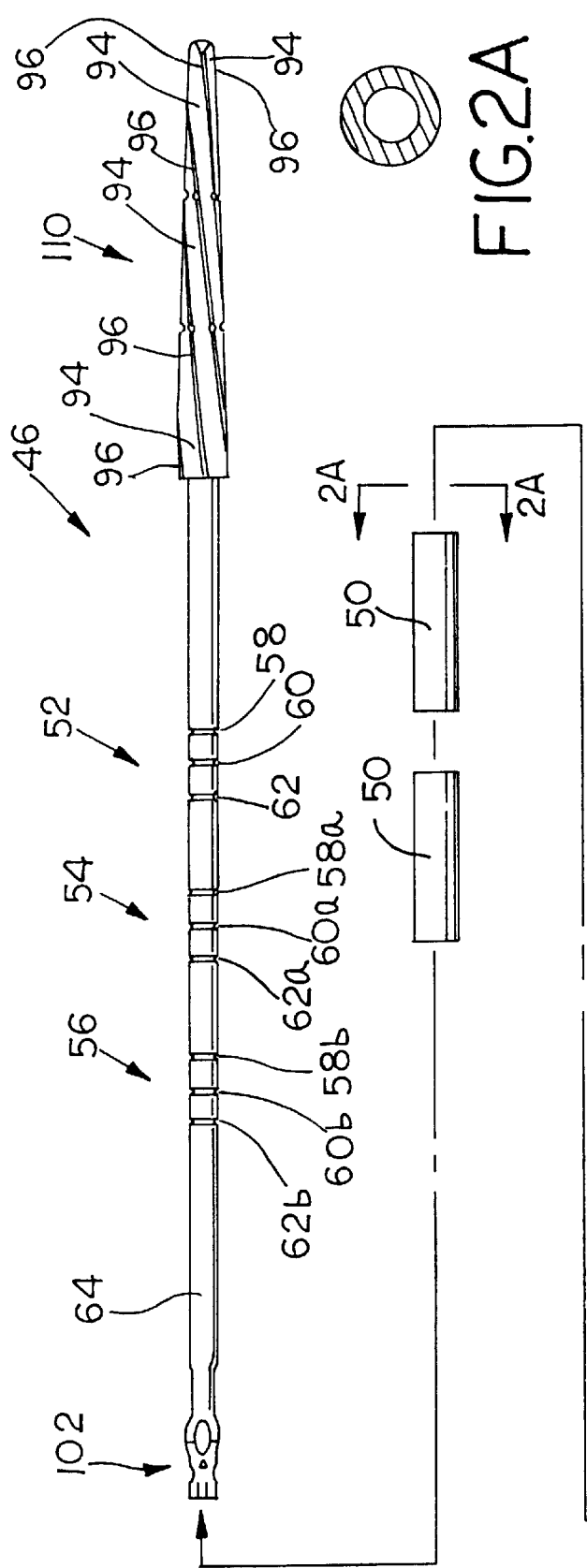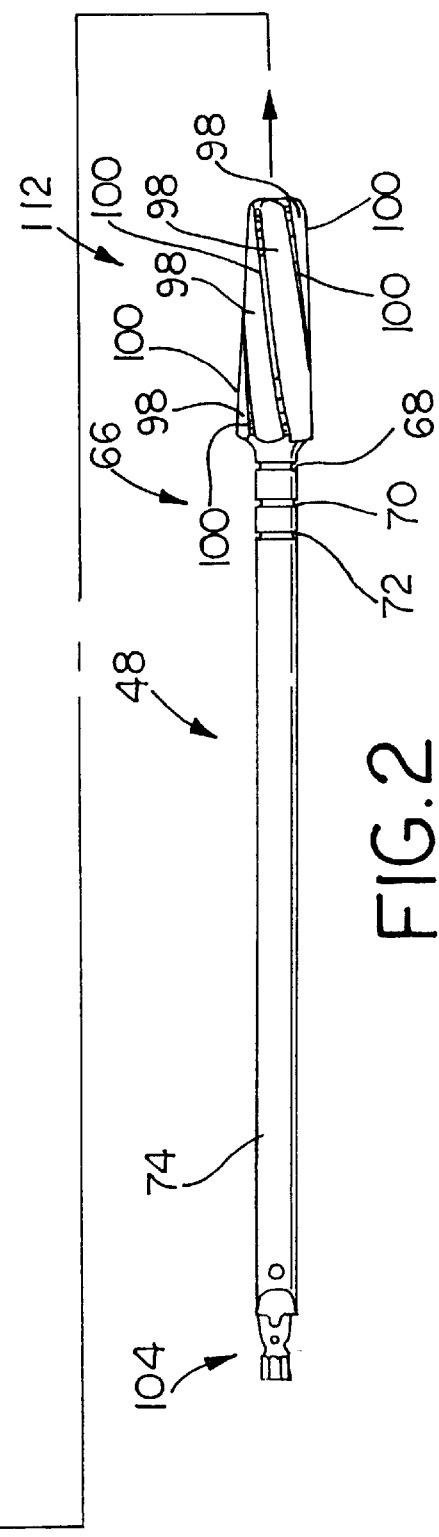

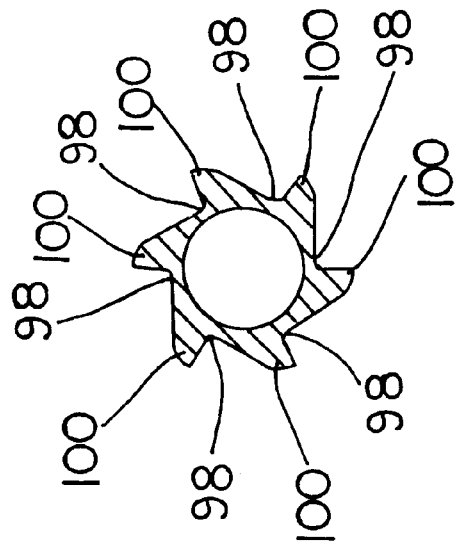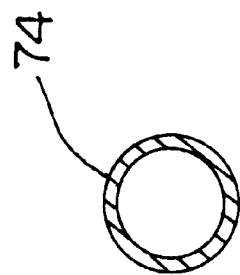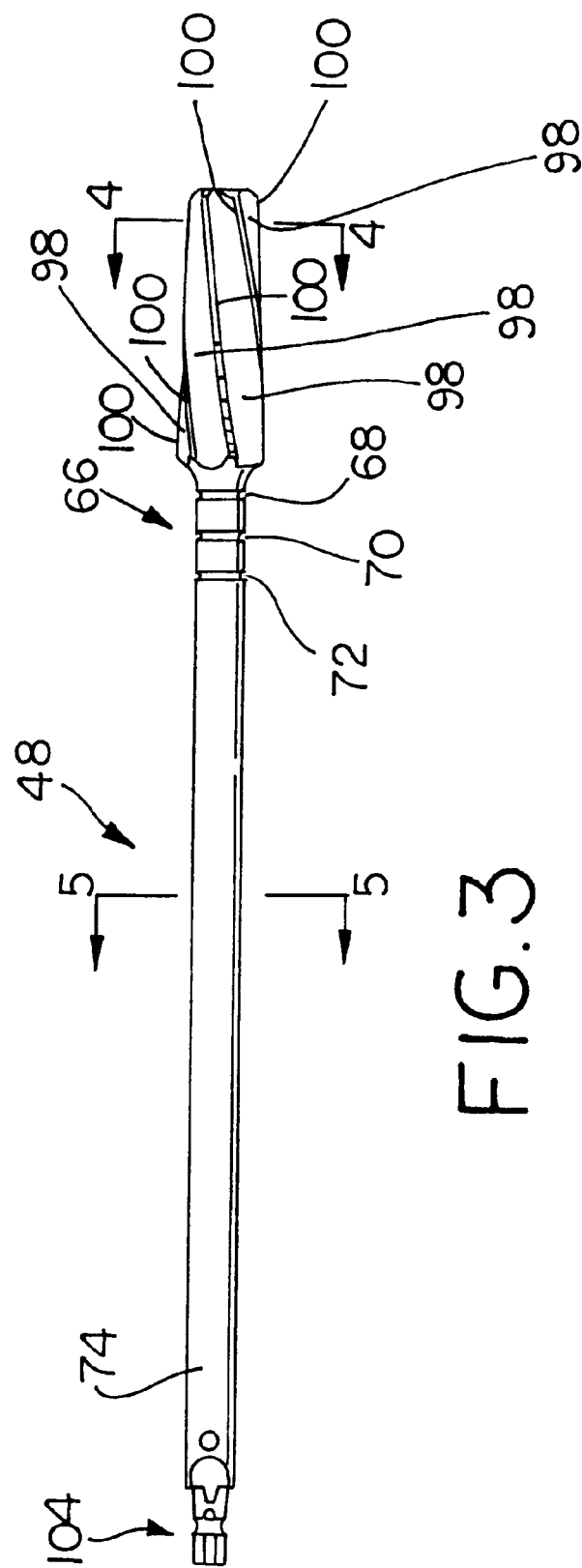

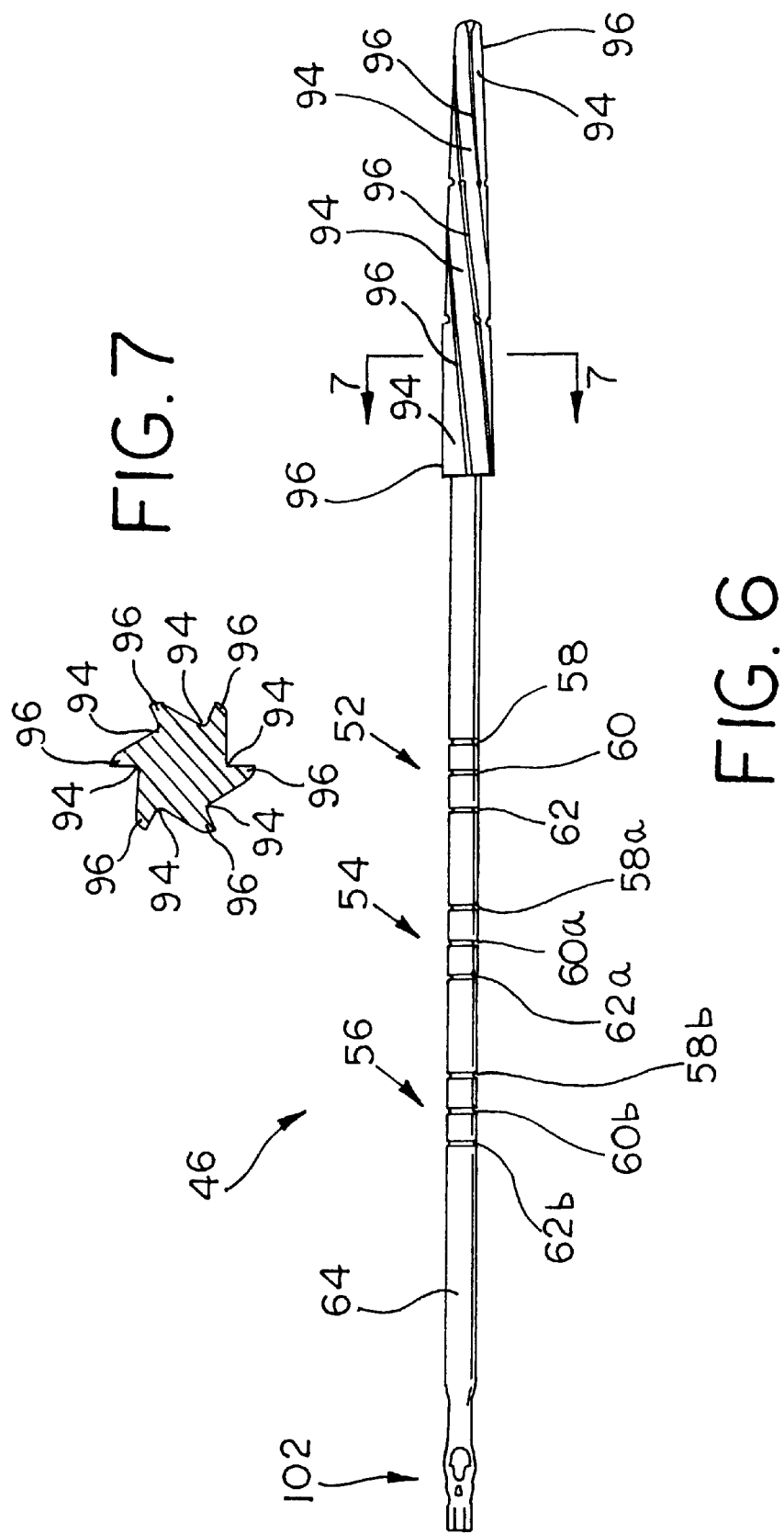

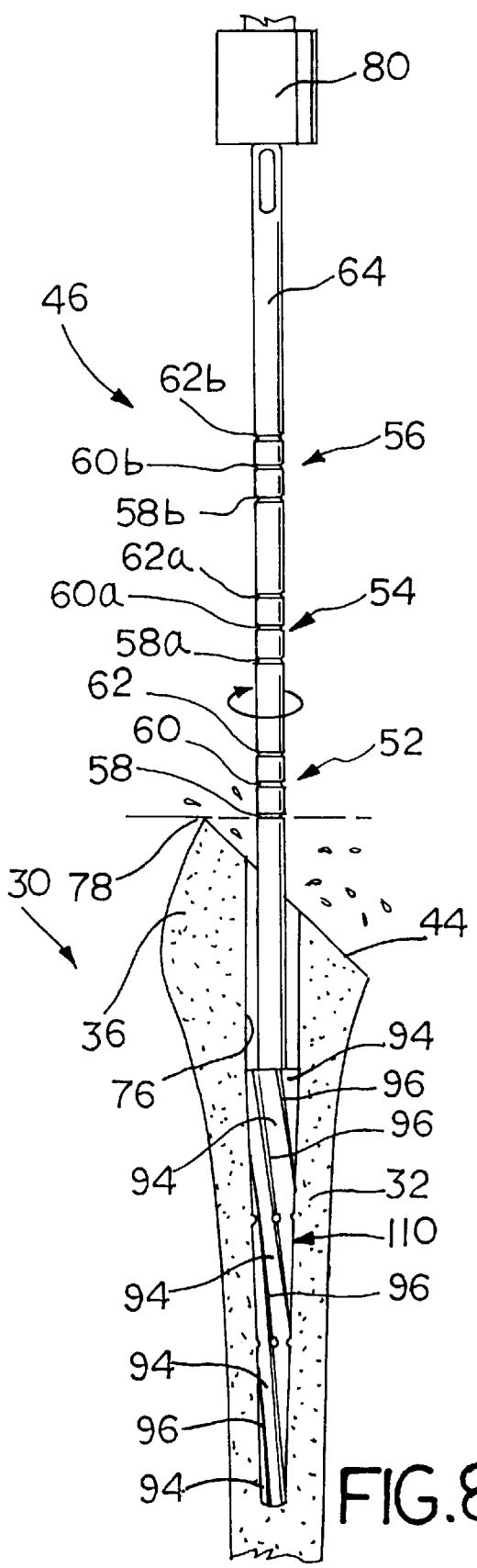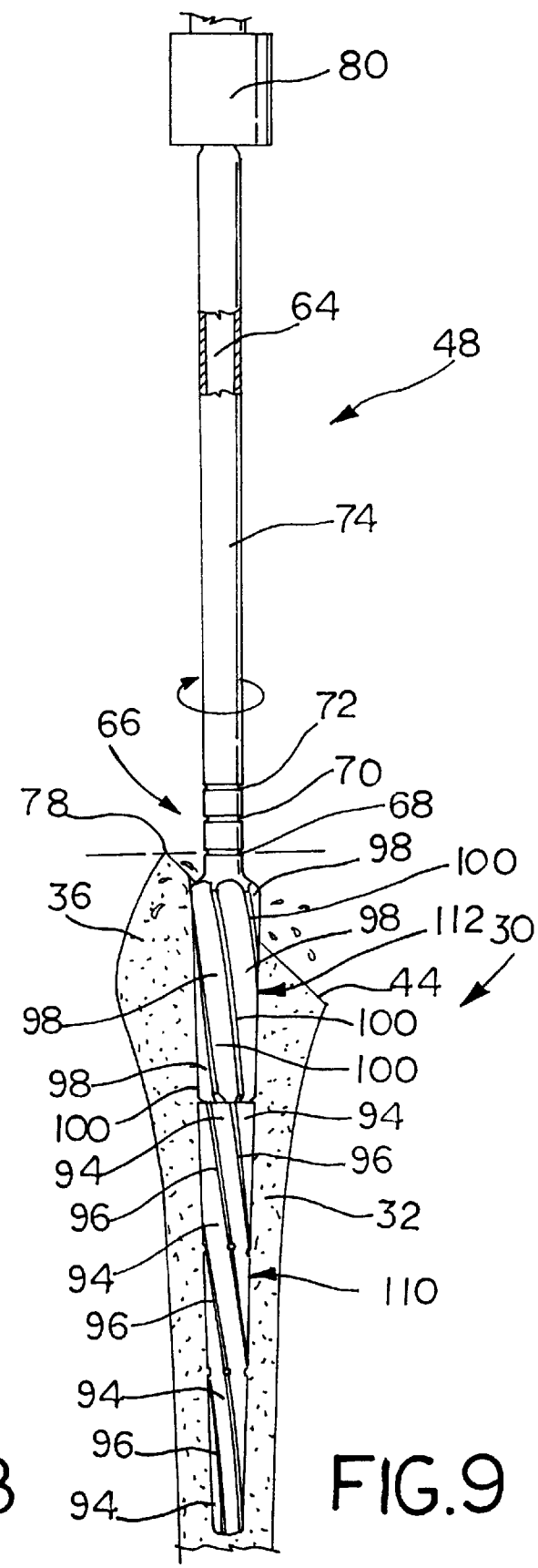

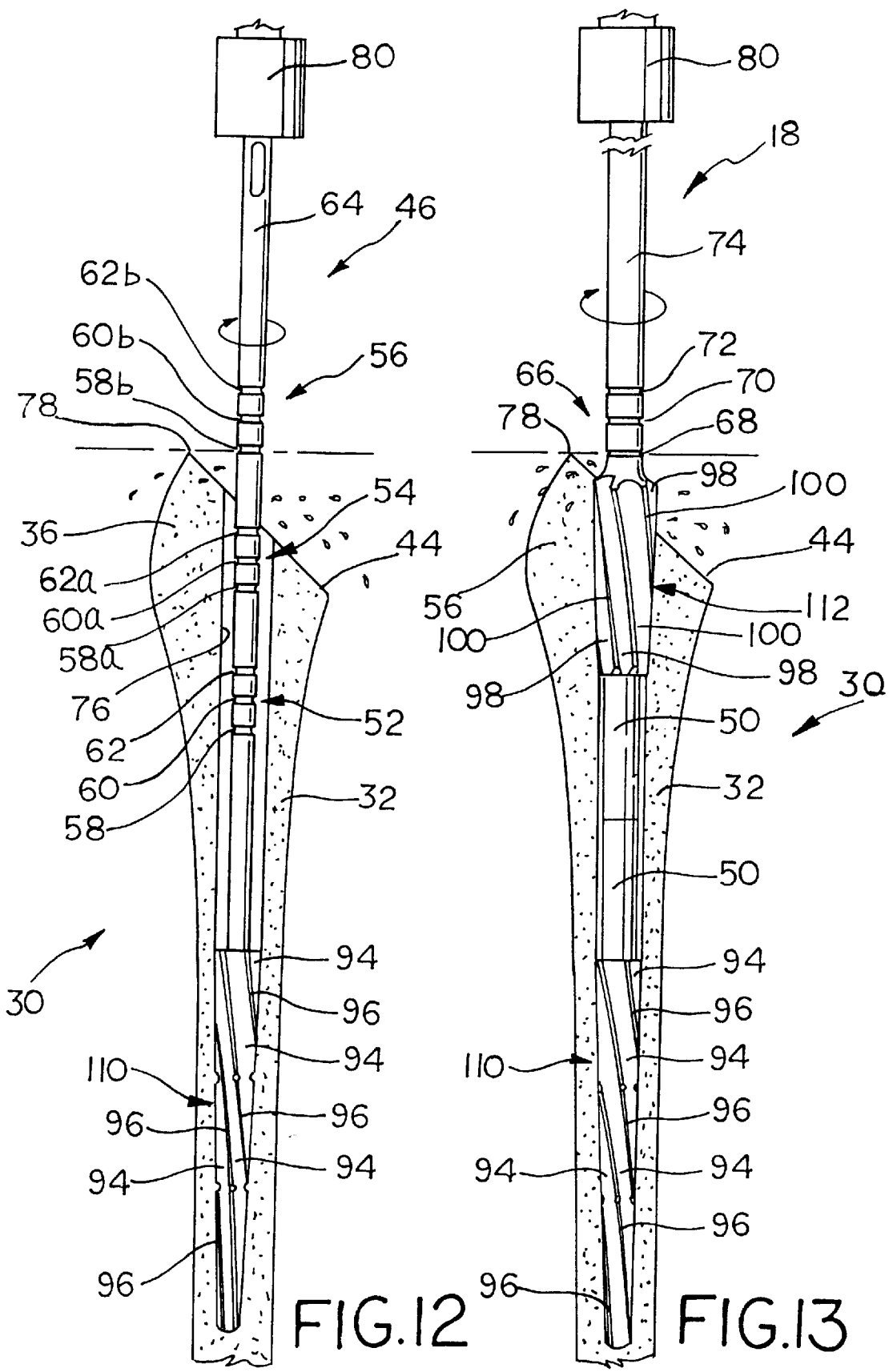

METHOD AND APPARATUS FOR PREPARING A FEMUR TO RECEIVE A MODULAR PROSTHETIC FEMORAL COMPONENT

BACKGROUND OF THE INVENTION

1. Field of the Invention

The present invention relates to a method and apparatus for preparing a femur to receive a prosthetic femoral component. More particularly, the present invention relates to a method and apparatus for preparing a femur to receive a modular prosthetic femoral component having a discrete proximal body and a discrete distal stem.

2. Description of the Related Art

Orthopaedic implants utilized to replace all, or a portion of, a patient's joint (e.g., the hip) are commonly utilized to restore the use of, or increase the use of a joint which has deteriorated due to, e.g., aging, illness, or injury. In the case of hip replacement, femoral components are utilized to replace a portion of the patient's femur including, e.g., the femoral head and neck. Prior to implantation of the femoral component, the patient's femur must be prepared to receive same.

Preparation of the femur entails excising a portion of the femur generally consisting of the femoral head and femoral neck (if this portion of the femur is intact). After removal of this portion of the femur, an elongate channel (i.e., femoral canal) of sufficient diameter to receive the prosthetic femoral component is formed in the femur. Typically, the elongate channel is formed utilizing a reamer to progressively bore through the femur until the desired depth is achieved. Some surgical techniques utilize a rasp either in addition to, or in lieu of reaming to prepare the femoral canal to receive the prosthetic femoral component. Many prosthetic femoral components are formed as an integral component having a femoral stem component sized whereby formation of the entire depth of the femoral canal with a single instrument, e.g., reamer, is appropriate.

In addition to the one-piece femoral components described above, modular femoral components utilizing a discrete proximal body together with a discrete distal stem have been developed. Such modular femoral components provide great flexibility to surgeons performing a total, or partial hip arthroplasty. Relatively few modular components may be utilized to form a relatively large number of versatile use femoral components. Furthermore, the modularity of these components allows for substantially infinite version adjustment when positioning the proximal body on an implanted distal stem. Modular femoral components are typically designed to achieve sufficient distal stem fixation in the femur (i.e., fixation of the distal stem to the femur) so that fixation of the proximal body is unnecessary. This is particularly advantageous in situations in which the femur has undergone extensive bone loss and therefore fixation of the proximal body is not possible.

Utilization of a modular femoral component requires that the proximal portion of the femoral canal be of larger diameter than the distal portion of the femoral canal. The distal portion of the femoral canal is generally sized so that the distal stem of the modular femoral component can be interference fit therein, while the proximal portion of the femoral canal is made large enough so that it will not interfere with the passage of the distal stem therethrough. Furthermore, many modular femoral components utilize a proximal body having a stem portion of greater diameter than the distal stem component. With this in mind, the proximal portion of the femoral canal must be of greater diameter to accommodate the proximal body. Additionally, it is desirable to size the proximal femoral canal to accommodate rotation of the proximal body about the distal stem (prior to affixation of the proximal body to the distal stem) so that version adjustment can be effected.

When utilizing modular prosthetic femoral components, imprecision in canal sizing can take the form of either over sizing, or under sizing. In cases of over sizing, portions of the femoral canal into which the distal stem will be seated will be oversized and, therefore, will not function to provide an interference fit with the distal stem. Since modular femoral components rely upon fixation of the distal stem, such over sizing is undesirable. Additionally, over sizing results in unnecessary bone removal. Under sizing is problematic because it will cause the distal stem to get hung up in the femoral canal prior to achieving the desired depth, which will make seating of the distal femoral component more difficult.

What is needed in the art is a method and apparatus for preparing a femur to receive a modular prosthetic femoral component which allows for precision in proximal and distal sizing.

SUMMARY OF THE INVENTION

The present invention provides an improved method and apparatus for preparing a femur to receive a modular prosthetic femoral component. A distal reamer is utilized to prepare the distal femoral canal and thereafter remains in the femoral canal during proximal sizing. The proximal canal sizing or forming tool, e.g. a reamer or rasp, is cannulated and is sized to fit about the shank of the distal reamer. Proximal sizing is effected with the distal reamer in place in the femur and a mechanical stop is utilized to control proximal sizing depth. The mechanical stop eliminates proximal over and under sizing. Preferably, the proximal sizing tool is a reamer.

The invention, in one form thereof, comprises an apparatus for preparing a femur to receive a modular prosthetic femoral implant. The apparatus of this form of the current invention includes a distal reamer having a distal reaming head and a shank as well as a cannulated reamer or rasp sized to fit about the shank of the distal reamer. A mechanical stop limits the travel of the cannulated reamer when the cannulated reamer is placed about the shank of the distal reamer.

The invention, in another form thereof, comprises, in combination, a modular prosthetic femoral implant set for replacing a portion of a femur and an apparatus for preparing the femur to receive a modular prosthetic femoral implant formed from the implant set. A distal femoral stem is seated in a femoral canal prepared by a pair of reamers. A distal reamer reams the femoral canal to receive the distal femoral stem and includes a distal reaming head and a shank. A cannulated reamer is sized to fit about the shank of the distal reamer and includes a proximal reaming head sized to ream a proximal portion of the femoral canal, whereby the distal femoral stem will pass through the proximal portion of the femoral canal without interference. A mechanical stop limits the travel of the cannulated reamer when the cannulated reamer is placed about the shank of the distal reamer. The mechanical stop prevents the cannulated reamer from reaming into an area of the femoral canal into which the distal femoral stem will be seated.

The invention, in yet another form thereof, comprises a method of preparing a femur to receive a modular prosthetic implant. The method of this form of the current invention includes the steps of: providing a distal reamer having a distal reaming head and a shank, the distal reamer having a mechanical stop associated therewith; reaming the femur with the distal reamer; providing a cannulated proximal sizing tool sized to fit about the shank of the distal reamer; with the distal reamer left in the femur, placing the cannulated sizing tool about the shank of the distal reamer; and advancing the sizing tool into the femur to form the proximal femoral canal to receive the proximal body component, whereby the mechanical stop limits the travel of the cannulated sizing tool.

The present invention advantageously eliminates the possibility of proximally over sizing or under sizing the femoral canal.

BRIEF DESCRIPTION OF THE DRAWINGS

The above mentioned and other features and objects of this invention, and the manner of attaining them, will become more apparent and the invention itself will be better understood by reference to the following description of an embodiment of the invention taken in conjunction with the accompanying drawings, wherein:

FIG. 2 is a radial elevational, exploded view of the reaming apparatus utilized in accordance with the present invention;

FIG. 2A is an axial elevational view of a reamer spacer in accordance with the present invention;

FIG. 3 is a radial elevational view of a proximal reamer in accordance with the present invention;

FIGS. 4 and 5 are sectional views thereof;

FIG. 6 is a radial elevational view of a distal reamer in accordance with the present invention;

FIG. 7 is a sectional view thereof;

FIG. 8 is a partial cut-away view illustrating insertion of the distal reamer;

FIG. 9 is a partial cut-away view illustrating insertion of the proximal reamer utilizing the reamer head of the distal reamer as a mechanical stop;

FIG. 12 is a partial cut-away view illustrating insertion of the distal reamer to accommodate insertion of the longest of a three piece distal femoral stem component set;

FIG. 13 is a partial cut-away view illustrating use of the proximal reamer with a pair of reamer spacers positioned to provide a mechanical stop therefor.

Figure 1:
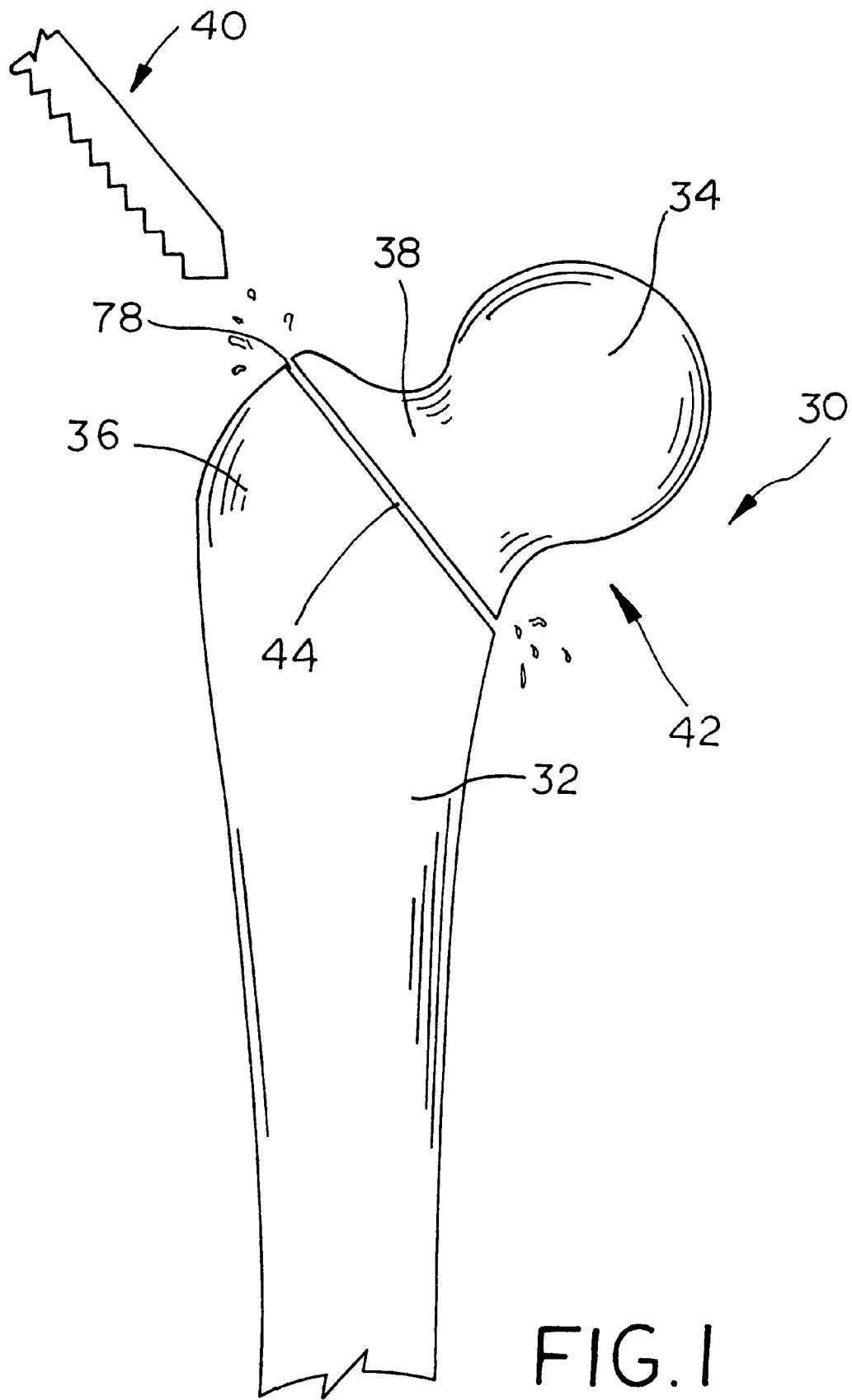
FIG. 1 is an elevational view of a femur.

Corresponding reference characters indicate corresponding parts throughout the several views. Although the drawings represent embodiments of the present invention, the drawings are not necessarily to scale and certain features may be exaggerated to better illustrate and explain the invention. The exemplification set out herein illustrates an exemplary embodiment of the invention only and such exemplification is not to be construed as limiting the scope of the invention in any manner.

DETAILED DESCRIPTION OF THE INVENTION

Referring now to the drawings and particularly to FIG. 2, there is illustrated distal reamer 46, reamer spacers 50, and proximal reamer 48. Reamer spacers 50 include longitudinal apertures sized to accommodate shank 64 of distal reamer 46. Similarly, proximal reamer 48 is cannulated and is sized to fit about shank 64 of distal reamer 46.

FIG. 1 illustrates femur 30 including femoral shaft 32, femoral neck 38, and femoral head 34. FIG. 1 illustrates preparation of femur 30 to receive a femoral implant in a primary implant procedure. Preparation of femur 30 entails excising cut portion 42 with femoral cutting tool 40 as illustrated in FIG. 1. Femoral cutting tool 40 is utilized to cut along cut line 44 for excision of cut portion 42. Cut line 44 is drawn from reference point 78 which is located atop greater trochanter 36. Generally, reference point 78 is located and an osteotomy guide is thereafter utilized to establish cut line 44. FIGS. 8–14 illustrate femur 30 after excision of cut portion 42. Modular prosthetic femoral components have applicability to both primary and revision surgeries as well as various instances in which significant bone loss has occurred. With this in mind, the above-described steps for excising cut portion 42 may be unnecessary, as this portion of femur 30 may no longer be present.

The method and apparatus of the current invention will hereinafter be described with respect to a modular prosthetic femoral implant set comprised, in part, of three distal femoral stems of graduated lengths, and three proximal bodies of graduated body heights. Distal reaming depth will, therefore, be a function of both the desired distal stem length as well as the desired proximal body height since the total length of the femoral component will be defined by the length of the distal stem combined with the height of the proximal body. Although described with respect to the above-described implant set, the apparatus of the current invention may be modified for use with implant sets having differing numbers of component parts.

FIGS. 8 and 9 illustrate use of distal reamer 46 and proximal reamer 48 to prepare femur 30 to receive a modular prosthetic femoral implant comprised, in part, of the shortest of three available femoral stems and the shortest of three available proximal bodies. As illustrated in FIGS. 2, 6, 8, 10, and 12, distal reamer 46 includes distal set of depth marks 52, intermediate set of depth marks 54, and proximal set of depth marks 56. Each set of depth marks includes distal indicator ring 58, intermediate indicator ring 60, and proximal indicator ring 62. Sets of depth marks 52, 54, and 56 correspond in number to the number of distal stems (i.e., three) offered with the prosthetic femoral component set utilized in accordance with this exemplary embodiment. Similarly, the number of indicator rings per set of depth marks corresponds in number to the number of proximal bodies (i.e., three) offered in the prosthetic femoral component set utilized in accordance with this exemplary embodiment. The sets of depth marks and indicator rings are utilized to determine the reaming depth of distal reamer 46.

When utilizing the shortest of the three distal stems, distal set of depth marks 52 is chosen. The appropriate indicator ring forming a part of distal set of depth marks 52 is next chosen based upon the height of the desired proximal body. For example, if the shortest proximal body is utilized, then distal ring 58 will be chosen as the appropriate indicator ring. Should the surgeon wish to utilize the shortest distal stem, and the intermediate length proximal body, then intermediate ring 60 would provide the appropriate depth indicator. Similarly, if the surgeon utilizes the shortest distal stem in conjunction with the tallest proximal body, then proximal ring 62 would provide the appropriate depth indication.

In cases in which the intermediate length distal stem is utilized, intermediate set of depth marks 54 provides the proper starting place for choosing the appropriate indicator ring. As with distal set of depth marks 52, indicator rings 58a, 60a, and 62a of intermediate set of depth marks 54 correspond to the shortest proximal body, the intermediate height proximal body, and the tallest proximal body, respectively. Finally, proximal set of depth marks 56 is utilized with the longest of the three available distal stems and includes indicator rings 58b, 60b, and 62b corresponding to the three available proximal body heights.

The distance between adjacent indicator rings of a set of depth marks is equal to the height differential between the corresponding proximal bodies. In this exemplary embodiment, the available proximal bodies have graduated body heights in ten millimeter increments, and, thus, adjacent indicator rings of a set of depth marks are separated by ten millimeters. Similarly, the available distal stems have graduated lengths in fifty millimeter increments, and, thus, adjacent sets of depth marks have a spacing of fifty millimeters between corresponding indicator rings. For example, proximal ring 62 of distal set of depth marks 52 is spaced fifty millimeters from proximal ring 62a of intermediate set of depth marks 54.

In use, the appropriate indicator ring of distal reamer 46 is aligned with top 78 of greater trochanter 36 to provide the appropriate distal reaming depth. The following chart indicates the appropriate indicator ring to be utilized with a distal stem/proximal body combination in accordance with the exemplary embodiment described herein. For purposes of the chart, S indicates the shortest component, I indicates the intermediate length component, and L indicates the longest component.

| DISTAL STEM | PROXIMAL STEM | SET OF DEPTH MARKS | INDICATOR RING |
|---|---|---|---|
| S | S | 52 | 58 |
| S | I | 52 | 60 |
| S | L | 52 | 62 |
| I | S | 54 | 58a |
| I | I | 54 | 60a |
| I | L | 54 | 62a |
| L | S | 56 | 58b |
| L | I | 56 | 60b |
| L | L | 56 | 62b |

FIGS. 8–13 illustrate use of distal reamer 46 and proximal reamer 48 to prepare femur 30 to receive various ones of distal stem 84 (FIG. 14) and proximal body 82 (FIG. 14) forming a part of the relevant modular femoral component set. FIG. 8 illustrates use of distal reamer 46 to prepare femur 30 to receive the shortest of three distal stems combined with the shortest of the three proximal bodies. Referring to FIGS. 2, 6, and 7 distal reamer 46 includes reaming head 110, shank 64, and driver end 102. Reaming head 110 includes flutes 94 and lands 96. As illustrated in FIG. 8, driver end 102 is operatively connected to driver 80 (e.g., a T-handle hand driver). Driver 80 is utilized to rotate distal reamer 46 and form femoral canal 76 in femoral shaft 32 of femur 30. Distal reamer 46 achieves a depth wherein distal ring 58 of distal set of depth marks 52 is aligned with reference point 78 atop greater trochanter 36. As illustrated in FIG. 9, proximal reamer 48 is thereafter inserted over shank 64 of distal reamer 46 with driver 80 operatively connected to driver end 104 of proximal reamer 48. As illustrated in FIGS. 2–5, proximal reamer 48 includes reaming head 112, shank 74, and driver end 104. Similar to distal reamer 46, reaming head 112 of proximal reamer 48 includes flutes 98 and lands 100. As illustrated in FIGS. 4 and 5, proximal reamer 48 is cannulated so that proximal reamer 48 may be placed about shank 64 of distal reamer 46.

In one exemplary embodiment, proximal reamer 48 includes depth marks 66 including distal depth mark 68, intermediate depth mark 70, and proximal depth mark 72. As illustrated in FIG. 9, reaming head 112 of proximal reamer 48 abuts reaming head 110 of distal reamer 46 when these instruments are utilized to prepare femur 30 to receive the shortest femoral stem. As illustrated in FIG. 9, depth marks 66 provide a check that the proper reaming depth has been achieved. Depth marks 72, 70, and 68 align with indicator rings 62, 60, and 58 when proximal reamer 48 achieves the appropriate depth.

Figure 10:
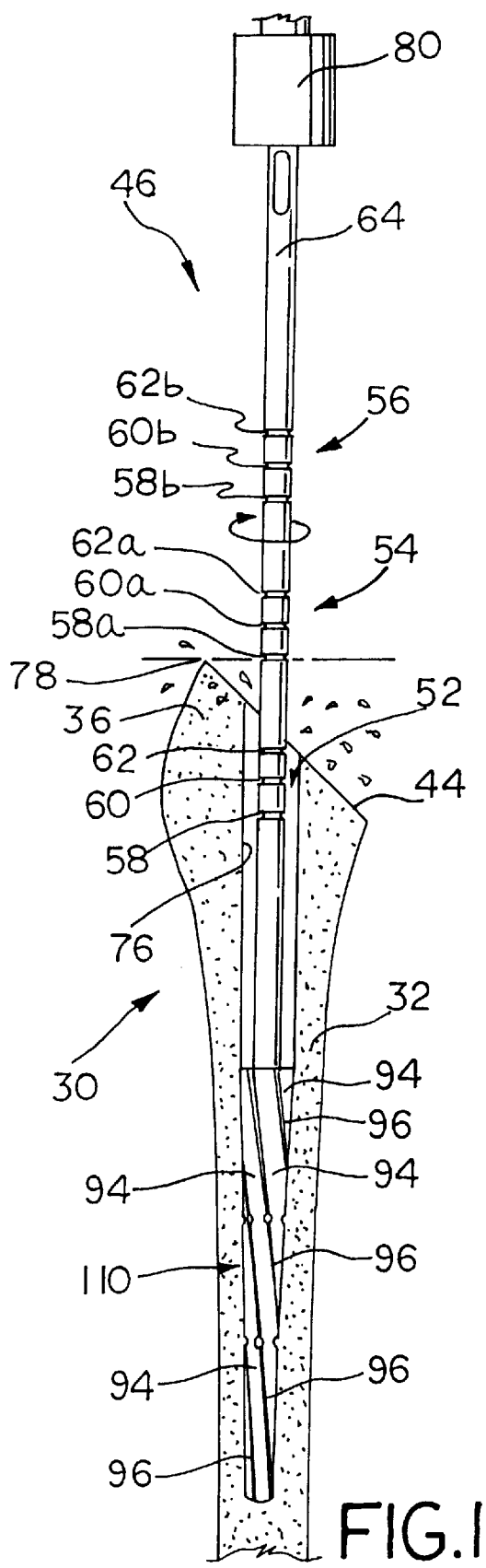
FIG. 10 is a partial cut-away view illustrating insertion of the distal reamer to an intermediate depth.
Figure 11:
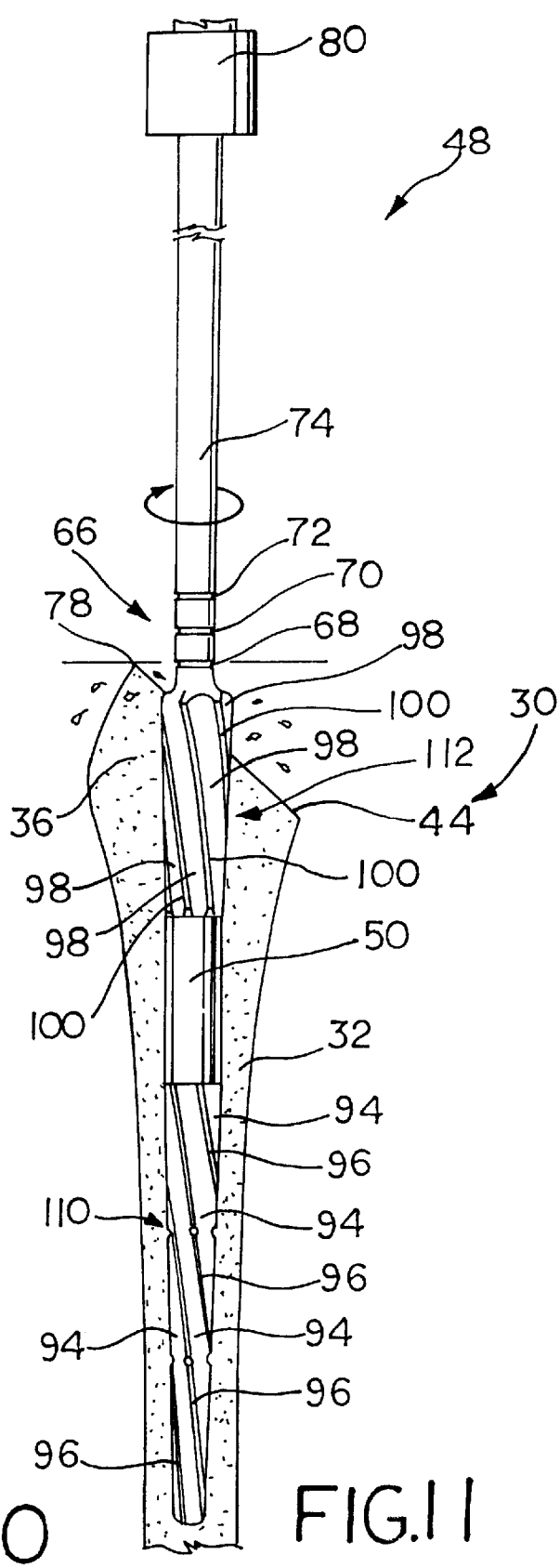
FIG. 11 is a partial cut-away view illustrating insertion of the proximal reamer, with a single reamer spacer utilized as a mechanical stop.

FIGS. 10 and 11 illustrate use of distal reamer 46 and proximal reamer 48 in conjunction with reamer spacer 50 to form femoral canal 76 in femoral shaft 32 of femur 30. As illustrated in FIG. 10, distal reamer 46 is positioned in femur 30 until achieving a depth wherein distal ring 58a of intermediate set of depth marks 54 is aligned with reference point 78 atop greater trochanter 36. As described above, indicator ring 58a corresponds to the use of the intermediate length distal stem in combination with the shortest proximal body. In this case, the spacing between the distal end of reaming head 112 of proximal reamer 48 and reaming head 110 of distal reamer 46 must be increased relative to the distance of these parts when utilizing the shortest of the distal stems. Reamer spacer 50 is utilized to account for this increased spacing and to provide a mechanical stop for proximal reamer 48. As illustrated in FIG. 2A, reamer spacer 50 is a hollow cylinder having an inner diameter sized whereby reamer spacer 50 can be placed about shank 64 of distal reamer 46. The outer diameter of reamer space 50 is of smaller size than the diameter reamed out by distal reamer 46.

Figure 14:
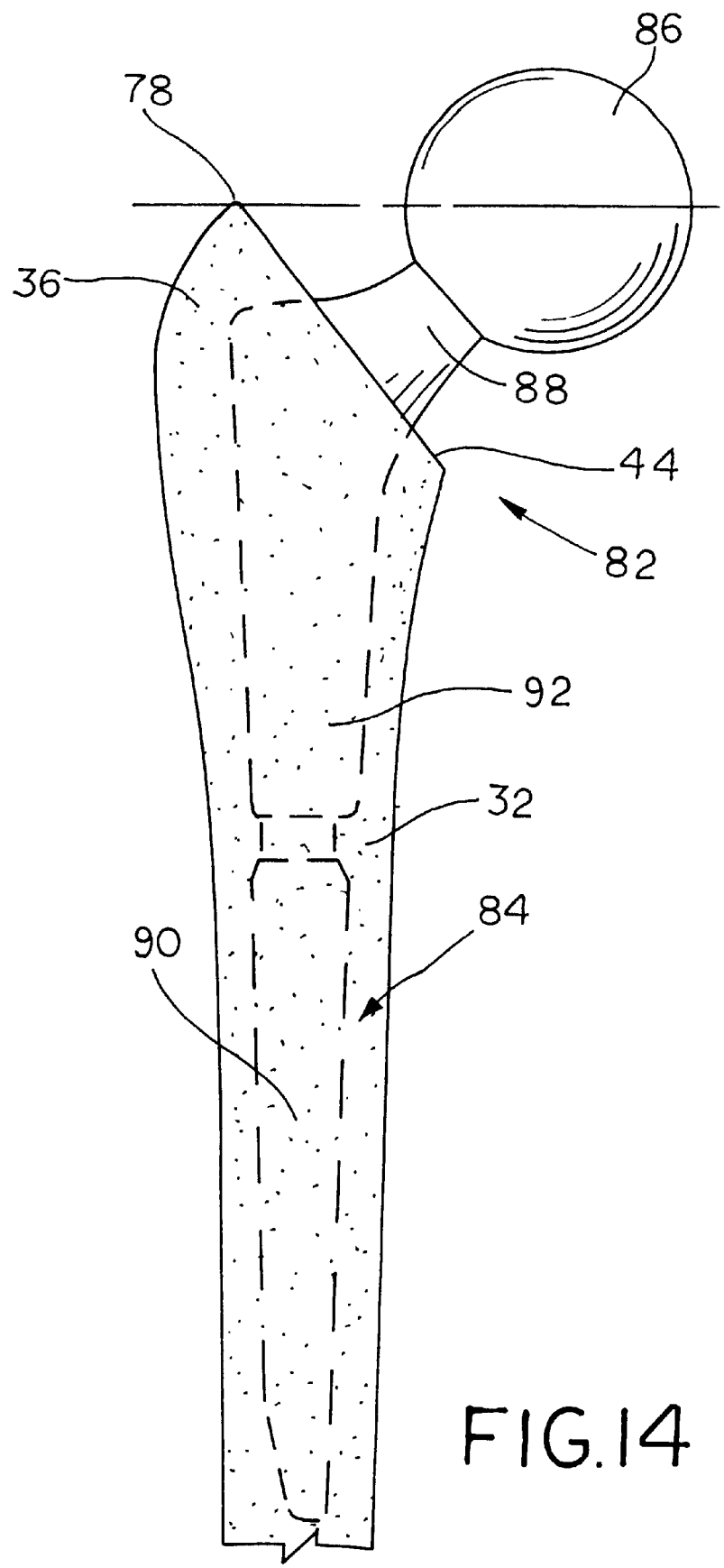
FIG. 14 is an elevational view illustrating a seated modular prosthetic femoral implant.

FIGS. 12 and 13 illustrate use of distal reamer 46 and proximal reamer 48 to prepare femoral canal 76 to receive a modular prosthetic femoral component formed, in part, from the longest of three available distal stems together with the shortest of three available proximal bodies. In this case, two reamer spacers 50 are utilized to provide the proper spacing between reaming head 112 of proximal reamer 48 and reaming head 110 of distal reamer 46. As described above, the three distal stems have graduated heights separated by fifty millimeters. Correspondingly, reamer spacers 50 have a height of fifty millimeters. FIGS. 8–13 illustrate preparation of femur 30 to receive a modular prosthetic femoral component including the shortest of three proximal bodies. Initial preparation of the femur to receive a prosthetic component including the shortest of three proximal bodies provides versatility in establishing proper leg length since leg length may be extended by utilizing a taller proximal body. Similarly, the surgeon may initially ream to a depth corresponding to use of the intermediate proximal body. In this case, leg length could, generally, be either increased or decreased via use of either the longer or the shorter proximal body, respectively. FIG. 14 illustrates an implanted modular prosthetic femoral component including distal stem 84 having distal femoral stem 90; proximal body 82 having proximal femoral stem 92, and femoral neck 88; and femoral head 86.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. An apparatus for preparing a femur to receive a modular prosthetic femoral implant, comprising:
   a distal reamer having a distal reaming head and a shank, wherein said distal reamer includes a plurality of sets of depth marks, each said set of depth marks being indicative of a reaming depth corresponding to one of a plurality of distal stems forming a part of a modular prosthetic femoral implant set;
   a cannulated forming tool sized to fit about said shank; and
   a mechanical stop for limiting the travel of said cannulated forming tool when said cannulated forming tool is placed about said shank.

2. The apparatus of claim 1, wherein the cannulated forming tool comprises a cannulated reamer.

3. The apparatus of claim 2, wherein said distal reaming head comprises said mechanical stop.

4. The apparatus of claim 2, further comprising:
   a reamer spacer sized to fit about said shank, said reamer spacer comprising said mechanical stop, said reamer spacer placed about said shank.

5. The apparatus of claim 2, wherein said cannulated reamer includes a proximal reaming head, said proximal reaming head operable to ream a proximal channel of a larger size than a distal channel reamed by said distal reaming head.

6. The apparatus of claim 1, wherein each of said set of depth marks comprises a plurality of indicator marks, each of said indicator marks being indicative of a reaming depth corresponding to one of a plurality of proximal bodies forming a part of said modular prosthetic femoral implant set.

7. The apparatus of claim 6, wherein each of said indicator marks comprises an indicator ring surrounding said shank of said distal reamer.

8. In combination, a modular prosthetic femoral implant set for replacing a portion of a femur and an apparatus for preparing the femur to receive a modular prosthetic femoral implant formed from said implant set, comprising:
   a distal femoral stem for affixation to the femur, said distal femoral stem being seated in a femoral canal;
   a distal reamer for reaming said femoral canal to receive said distal femoral stem, said distal reamer having a distal reaming head and a shank, wherein said distal reamer includes a plurality of sets of depth marks, each said set of depth marks being indicative of a reaming depth corresponding to one of a plurality of distal femoral stems forming a part of the modular prosthetic femoral implant set, said distal femoral stem being chosen from said plurality of distal femoral stems;
   a cannulated reamer sized to fit about said shank, said cannulated reamer having a proximal reaming head sized to ream a proximal portion of said femoral canal, whereby said distal femoral stem will pass through said proximal portion of said femoral canal without interference; and
   a mechanical stop for limiting the travel of said cannulated reamer when said cannulated reamer is placed about said shank of said distal reamer, whereby said mechanical stop prevents said cannulated reamer from reaming into an area of the femoral canal into which the distal femoral stem will be seated.

9. The combination of claim 8, wherein said distal reaming head comprises said mechanical stop.

10. The combination of claim 8, further comprising a reamer spacer sized to fit about said shank, said reamer spacer placed about said shank, said reamer spacer comprising said mechanical stop.

11. The combination of claim 8, further comprising a proximal femoral component for affixation to said distal femoral stem.

12. The combination of claim 8, wherein each of said set of depth marks comprises a plurality of indicator rings, each of said indicator rings being indicative of a reaming depth corresponding to one of a plurality of proximal bodies forming a part of the modular prosthetic femoral implant set.

13. A method of preparing a femur to receive a modular prosthetic implant, comprising:
   providing a distal reamer having a mechanical stop associated therewith, said distal reamer further comprising a distal reaming head, a shank, and a plurality of sets of depth marks, each said set of depth marks being indicative of a reaming depth corresponding to one of a plurality of distal stems forming a part of a modular prosthetic femoral implant set;
   choosing a distal femoral stem;
   choosing one of said sets of depth marks corresponding to said distal femoral stem;
   reaming the femur with said distal reamer to a depth wherein the chosen set of depth marks is aligned with a reference point;
   providing a cannulated sizing tool sized to fit about the shank of said distal reamer;
   with the distal reamer left in the femur, placing the cannulated sizing tool about said shank; and
   advancing the cannulated sizing tool to form a proximal femoral canal in the femur, whereby said mechanical stop limits the travel of said cannulated sizing tool.

14. The method of claim 13, wherein the step of providing a cannulated sizing tool comprises providing a cannulated reamer, and the step of placing the cannulated sizing tool about said shank comprises placing the cannulated reamer about said shank, and the step of advancing the cannulated sizing tool to form a proximal femoral canal in the femur comprises reaming the femur with said cannulated reamer.

15. The method of claim 14, wherein said distal reaming head comprises said mechanical stop.

16. The method of claim 14, further comprising the steps of:
   providing a reamer spacer sized to fit about the shank of said distal reamer; and
   placing said reamer spacer about said shank before placing said cannulated reamer about said shank, whereby said reamer spacer comprises said mechanical stop.

17. A method of preparing a femur to receive a modular prosthetic implant, comprising:
   providing a distal reamer, wherein said distal reamer includes a plurality of sets of depth marks, each said set of depth marks being indicative of a reaming depth corresponding to one of a plurality of distal femoral stems forming a part of a modular prosthetic femoral implant set, each said set of depth marks comprising a plurality of indicator marks, each of said indicator marks being indicative of a reaming depth corresponding to one of a plurality of proximal bodies forming a part of the modular prosthetic implant set, said method further comprising:

choosing a distal femoral stem;

choosing a proximal body for affixation to said distal femoral stem;

choosing one of said sets of depth marks corresponding to said distal femoral stem;

choosing one of said indicator marks forming a part of said chosen set of depth marks said chosen indicator mark corresponding to said proximal body; and wherein said step of reaming the femur with said distal reamer comprises reaming the femur with said distal reamer to a depth wherein the chosen indicator mark is aligned with a reference point.

18. The method of claim 17, further comprising:

seating the chosen distal femoral stem in the femoral canal formed by said reaming steps; and affixing the chosen proximal body to said distal femoral stem.

19. The method of claim 13 or 17, wherein said reference point comprises the tip of the greater trochanter of the femur.

* * * * *